United States Patent [19]
De Luca

[11] Patent Number: 4,581,752
[45] Date of Patent: Apr. 8, 1986

[54] X-RAY SHADOW PREVENTION DEVICE

[76] Inventor: James T. De Luca, 530 Old Country Rd., Westbury, N.Y. 11590

[21] Appl. No.: 607,708

[22] Filed: May 7, 1984

[51] Int. Cl.⁴ .................. A61B 6/00; A41D 27/26; H05G 1/00

[52] U.S. Cl. ................................ 378/62; 2/267; 378/204

[58] Field of Search ............ 378/204, 62, 182, 184, 378/167, 171, 210; 2/267; 15/244 B, 244 C

[56] References Cited

U.S. PATENT DOCUMENTS

| | | | |
|---|---|---|---|
| 2,394,419 | 2/1946 | Zimmerman | 15/244 C |
| 3,135,961 | 6/1964 | Roderick | 2/267 |

Primary Examiner—Bruce C. Anderson
Assistant Examiner—T. N. Grigsby
Attorney, Agent, or Firm—Charles E. Temko

[57] ABSTRACT

An X-Ray Shadow Prevention Device for use in the taking of chest exposures for the prevention of the formation of shadows on the exposed film caused by contact of the nipples of the patient with the surface of the X-ray film-holder. The device includes a resilient layer of foam rubber or the equivalent which deforms upon contact with the patient, and prevents the forming of a quasicircular air space surrounding the nipples which cause a correspondingly-shaped shadow to appear on the film.

5 Claims, 6 Drawing Figure

X-RAY SHADOW PREVENTION DEVICE

BACKGROUND OF THE INVENTION

This invention relates generally to the field of radiology, and more particularly to an improved means for preventing the formation of false images upon exposures of X-ray film which may be the subject of misinterpretation.

When making an X-ray exposure of the chest, the patient is normally positioned standing adjacent a film-holder. As the patient leans forward and comes into contact with the film-holder, the nipples, male or female, are pressed against the generally planar exposed surface of the film-holder. In some cases, the resultant pressure will cause the nipple to appear as a small nodule on the final film product or chest-X-ray. The shadow may so resemble an early cancer or benign disease process that a radiologist interpreting the film will feel compelled to repeat the exposure with the placing of lead markers on the nipples so as to be reassured that the observed images is in fact a nipple shadow rather than a tumor or other process.

The shadow is caused by the fact that the nipple normally protrudes outwardly of the surrounding areola, and upon contacting a planar surface, an arcuately shaped air space is created which registers as a shadow on the film.

SUMMARY OF THE INVENTION

Briefly stated, the invention contemplates the provision of a deformable generally planar shield interposed between the patient and the film-holder which will at least partially conform to the pectoral area of the patient, and thereby prevent the formation of air spaces surrounding the nipples which result in false imaging upon the film. The shield may take the form of a rectangular pad which may be attached to the film holder, or alternatively, incorporated into a gown, vest or bib worn by the patient at the time of X-ray exposure. Depending upon considerations of convenience and cost, the shield may be manufactured in disposable form of fibrous material, and synthetic resinous foam, or of more permanent textile materials.

BRIEF DESCRIPTION OF THE DRAWING

In the drawing, to which reference will be made in the specification, similar reference characters have been employed to designate corresponding parts throughout the several views.

DETAILED DESCRIPTION OF THE DISCLOSED EMBODIMENTS

Figure 1:
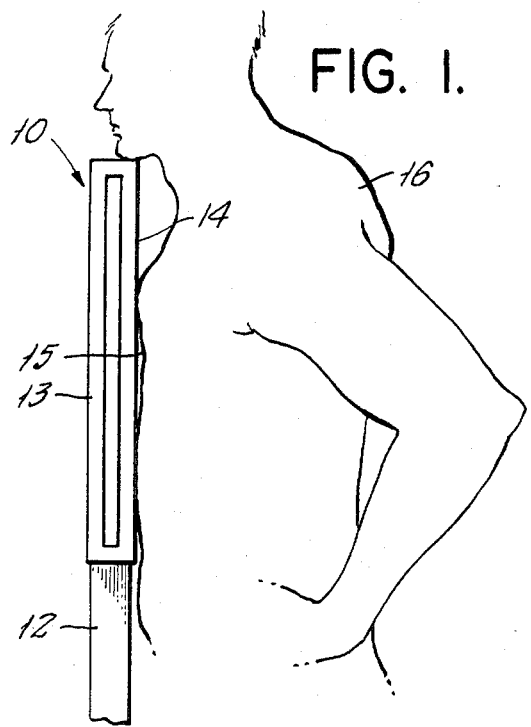
FIG. 1 is a view in elevation of a typical X-ray installation in common use in the art.

In accordance with the invention, reference character 10 designates a known X-ray exposure installation, including a film stand 11 positioned upon a support member 12 and accommodating a film-holder 13 having an outer planar surface 14 against which the chest 15 of a patient 16 is pressed during exposure.

While the above described problem does not necessarily occur each time an exposure is made, depending upon the amount of pressure applied, and the configuration of the individual patient, distortion of the nipples under pressure causes the formation of an air gap in the area of the areola which causes a correspondingly shaped shadow to appear when the film is processed. It is the purpose of the invention to provide a means for preventing the formation of the air gap, thereby preventing the occurrence of the image on the film.

Figure 2:
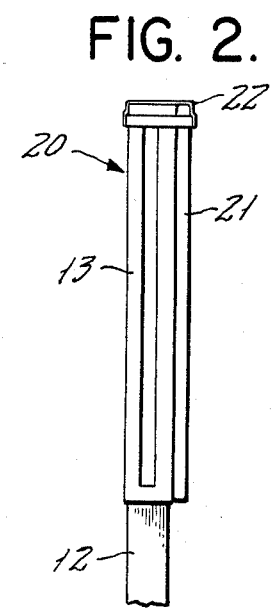
FIG. 2 is a corresponding schematic view in elevation showing a first embodiment of the invention in installed condition.
Figure 3:
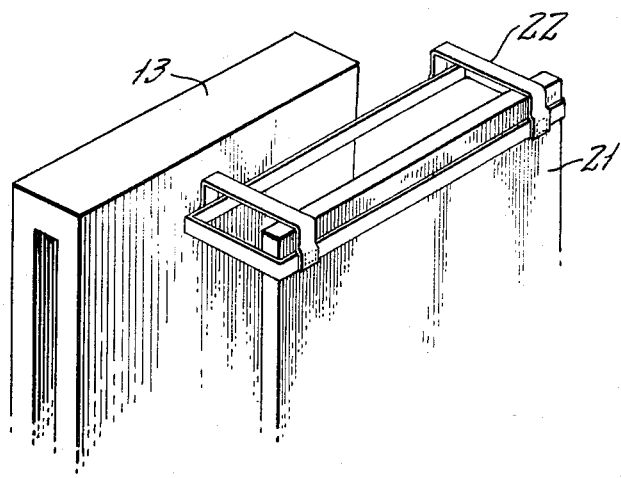
FIG. 3 is a view in perspective of a first embodiment.

FIG. 2 illustrates a first embodiment of the invention, generally indicated by reference character 20, which comprises a rectangular pad element 21, preferably of synthetic resinous foam, and having an attaching harness 20 which enables it to be secured either to the film-holder or the support member 12. In preferred configuration, the pad is approximately seventeen inches high, fourteen inches wide, and one-half inch thick, although the thickness will vary depending upon the density of the foam from which it is made. When in use, the patient is pressed against the pad, rather than the surface of the film-holder, and the pad distorts to accommodate to the configuration of the individual nipple, and fills in any air space which might otherwise be formed.

Figure 4:
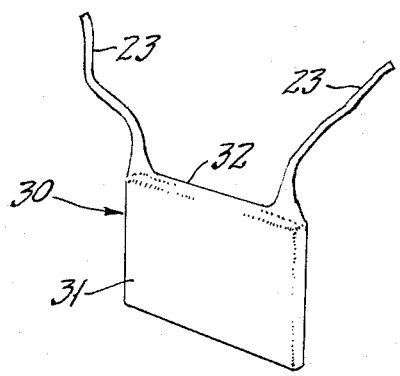
FIG. 4 is a view in elevation of a second embodiment of the invention.

Referring to FIG. 4, a second embodiment, generally indicated by reference character 30 is in the form of a rectangularly shaped bib. The bib includes a rectangular panel 31, of textile or non-woven fabric, bounded by an upper edge 32 to which a pair of tie strings 23 are attached. Secured to an inner surface 34 are a pair of discs 35 of mono or multi-layered foam 35 positioned to overlie the nipples of the wearer.

Figure 5:
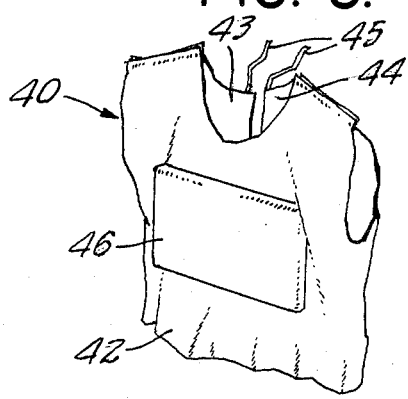
FIG. 5 is a view in elevation showing a third embodiment of the invention.

Referring to FIG. 5, a third embodiment 40 is in the form of a rear opening gown including a front panel 42 and rear panels 43 and 44 interconnected by ties 45. The pad 46 is secured to the outer surface of the panel 42 by cementitious means (not shown).

Figure 6:
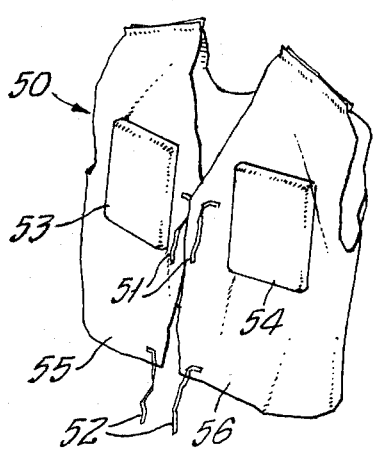
FIG. 6 is a view in elevation showing a fourth embodiment of the invention.

FIG. 6 illustrates a fourth embodiment of the invention, generally indicated by reference character 50, in the form of a front opening gown closed by ties 51. The pads 53 and 54 are secured to an outer surface of the front panel.

I wish it to be understood that I do not consider the invention limited to the precise details of structure shown and set forth in this specification, for obvious modifications will occur to those skilled in the art to which the invention pertains.

I claim:

1. In the method of taking a chest X-ray which includes the steps of providing a film-holder having a sensitive film therein, providing means for supporting said film-holder in relatively fixed position, placing a patient in position with chest pressed against an outer surface of said holder, and exposing said film holder to X-rays projected through said patient; the additional step of providing a layer of soft resilient material capable of confirming to the shape of the nipples of the patient, and positioning the same between the chest and said surface of said film holder, whereby to prevent the formation of air spaces surrounding the nipples capable of forming an image on said sensitive film disposed within said holder during X-ray exposure.

2. The method in accordance with claim 1, in which said resilient material is natural or synthetic resinous foam rubber.

3. A device for preventing the forming of images upon x-ray film during exposure caused by distortion of the nipples of a patient pressed against a film-holder containing said film, thereby forming an airspace surrounding the nipple, said device comprising: a bib-like garment, including a plainar member, a pair of resilient foam pads, capable of conforming to the configuration of said nipples secured to a surface of said planar member, and tie strips for supporting said plainar member upon the chest of a patient.

4. A device for preventing the forming of images upon x-ray film during exposure caused by distortion of the nipples of a patient pressed against a film-holder containing said film, thereby forming an airspace surrounding the nipple, said device comprising: two resilient foam pads, a vest including a pair of front panels, each of said pads secured to ourter surface of one of said front panels.

5. A device for preventing the forming of images upon x-ray film during exposure caused by distortion of the nipples of a patient pressed against a film-holder containing said film, thereby forming an airspace surrounding the nipple, said device comprising: a rear opening gown, including a continuous front panel, and a foam pad capable of conforming to the configuration of said nipples secured to an outer surface of said front panel.

* * * * *